United States Patent [19]

Martin

[11] 4,392,827
[45] Jul. 12, 1983

[54] SELF-CONTAINED ROOT CANAL HEATED CONDENSER DENTAL INSTRUMENT

[76] Inventor: Howard Martin, 909 Pershing Dr., Silver Spring, Md. 20910

[21] Appl. No.: 318,069

[22] Filed: Nov. 4, 1981

[51] Int. Cl.³ ............................................. A61C 3/00
[52] U.S. Cl. ...................................... 433/32; 433/224
[58] Field of Search ................................. 433/224, 32

[56] References Cited

U.S. PATENT DOCUMENTS

| | | | |
|---|---|---|---|
| 1,792,121 | 2/1931 | Pieper | 433/32 |
| 3,841,311 | 10/1974 | Brown | 433/32 |
| 3,899,830 | 8/1975 | Malmin | 433/224 |

*Primary Examiner*—Robert Peshock
*Attorney, Agent, or Firm*—Walter G. Finch

[57] ABSTRACT

The invention is an improved dental instrument for root canal condensation dental work. The instrument is self-contained in that it is a combination tool used as a spreader, a condenser, and a filling material heating unit, each of which is alternately and/or concurrently useable while inserted within the root canal structure of a patient. The invention provides several embodiments, each of which comprises: a plugger component (which use combines the functions of a spreader, a condenser, and a material heating unit); a handle component affixed to the plugger component; a power supply component for producing heat; and a transmission component for transmitting heat produced by the power supply component to the material heating unit of the plugger component. The transmission component has a conveniently located finger operation switch to interrupt the power supply and cut off the flow of heat. The plugger component is provided in a range of sizes to fit the range of internal sizes in different parts of the root canal.

8 Claims, 10 Drawing Figures

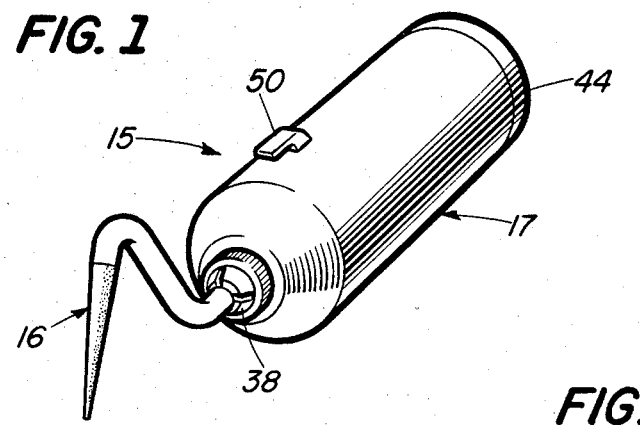
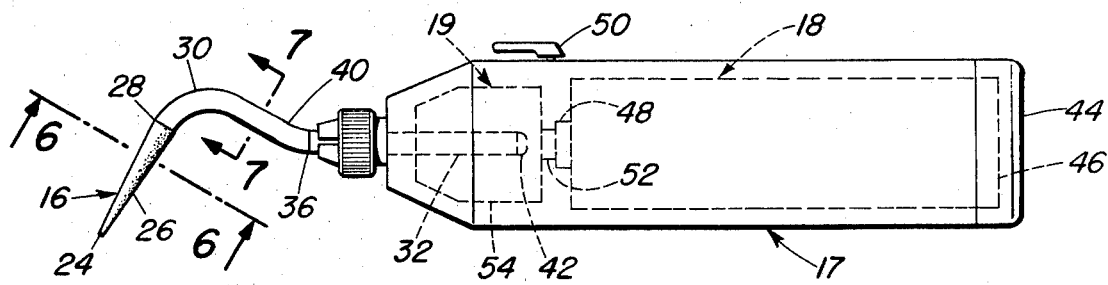
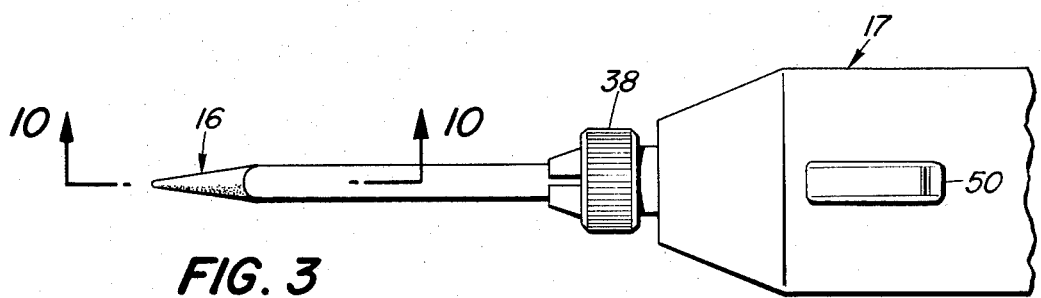
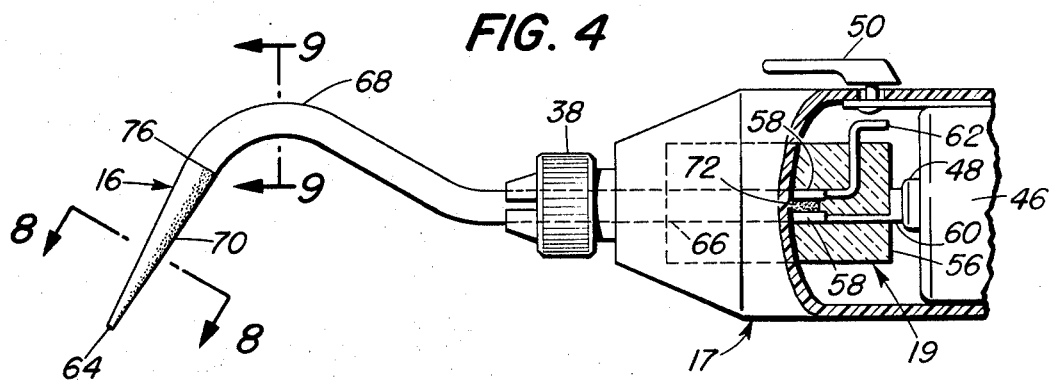

SELF-CONTAINED ROOT CANAL HEATED CONDENSER DENTAL INSTRUMENT

BACKGROUND AND SUMMARY OF THE INVENTION

The invention relates to dental treatment equipment and in particular to root canal dental instruments. Specifically, it relates to a self-contained root canal dental instrument that combines the operations of a root canal spreader, a root canal condenser, and a root canal filling material heater.

A need has existed for a long time for a way to reduce the time involved in filling a prepared root canal of a human tooth with the filling material. The time involved being used in the continual pick up of separate dental tools for spreading filling material, condensing the filling material, and the alternate heating and reheating of the filling material, during the spreading and condensing operations. This invention eliminates the problems and reduces the time, thus effectively reducing the cost of root canal work.

Gutta percha is the usual root canal filling material that is used for filling root canals. However, it is to be understood that this invention is usable on other root canal filling materials that are spread and condensed in the root canal and which are heated to improve the flow qualities of the root canal filling material.

The gutta percha material deforms when warmed and compressed. It becomes pliable at 25° to 30° Celsius, it becomes soft at 60° Celsius, and it decomposes at 100° Celsius. At such temperatures phase transition occurs allowing the gutta percha to flow into the many irregularities of the prepared root canal, thus allowing for a three-dimensional obturation and sealing to occur. Such a three-dimensional obturation and sealing is necessary for success in root canal therapy.

When the filling material, such as gutta percha, is softened, it is then compressed into the numerous aberrations of the root canal in order to effectively seal the root canal cavity. The compressing of the filling material in the prior art is performed by using root canal filling spreaders and filling condensers of a variety of sizes and with several handle designs (both long and short).

The filling spreaders and condensers of the prior art for root canal work are generally of stainless steel or chromium plated brass. The filling spreaders are smooth, flat ended and slightly tapered.

In use in the prior art, the root canal filling spreaders and condensers have to be heated over a flame, such as over the flame of a Bunsen burner, and then passed into the mouth of a dental patient and then into the prepared root canal where the filling material, such as gutta percha, has been placed. There is the constant danger of burning the patient about the mouth each time a heated dental tool is moved from the flame to inside the mouth. The present invention reduces the number of entries into the mouth that are necessary during a root canal filling, and also provides for inducing the heat for the tool after the tool is in the tooth at the root canal cavity.

Once a first portion of filling material is in the root canal, the filling spreaders are used to heat the filling material and then laterally condense or press the filling material into the root canal areas. Thereafter, a filling condenser is used to maintain the heat or reheat the filling material and to vertically condense the filling material into the root canal. This is a compacting type of operation. While the use of the filling condenser to vertically condense the filling material is often referred to as a plugging operation, the use of the filling spreader to laterally condense the material before the vertical condensing is also a part of the total plugging operation.

Additional bits or points of filling material are placed into the root canal cavity and then followed by the spreading and condensing operations described hereinbefore for the filling spreader and condenser root canal tools. These operations are continued until the required amount of filling material plugs and seals the root canal in accordance with dental art. However, it is to be noted that the repeated changes between filling spreader and filling condenser and the continual reheating of the dental tools increases the risk in the prior art of burning the patient as noted hereinbefore.

Regarding the gutta percha, or any similar filling material, the deformation under heat and stress allows compaction and condensation that leads to the lateral spreading to fill the voids in the root canal. As bits or points of filling material are placed into the root canal, as hereinbefore described, the heated spreader tool is forced between the bits or points of material after each such insertion which pushes the filling material to the apex of the root canal and, concurrently, laterally. The tool is pressed manually and also rotated side to side to achieve the spreading of the material.

It is to be noted that in this prior art the heated filling spreader, and also the heated filling condenser, must be transported quickly from the Bunsen burner into the mouth of the patient and into the tooth and the root canal and against the cold mass of filling material. The present invention reduces these numerous reheating and transport movements.

If hot enough, the filling material will not stick to the dental tools of the prior art. If the filling material retains the heat a cold filling condenser may be used to perform the plugging operation, however, this cold operation also tends to cool the filling material which then requires a reheating. However, general practice also shows that a small amount of the filling material often adheres to the dental tools. The present invention eliminates this condition as well as many of the repeated tool exchanges and reheating operations.

In the prior art some attempts have been made to provide for heating the tools while in the mouth. Problems encountered have been that the tips have been bulky and too wide, requiring some use of the old prior art tools mentioned hereinbefore. Also, the tips do not wedge lock into place and 360° rotation has been encountered which reduces the effectiveness of the condensing operation.

The heat control has been unreliable, the system having as many as ten dial settings which required an assistant or required the dentist to stop the condensing operations to attempt to make a better heat selection or to interrupt the heat process.

In addition to the above problems, the filling material sticks to the surface of the socalled heat control tools, and the system has a cumbersome power box and control means.

In the medical/dental profession a self-contained cautery, used for cauterizing, is usable only for cauterizing and is not usable for root canal work, it is also bulky.

In the present invention, the self-contained root canal instrument is provided in a range of sizes of small plugger components for use from the area of the apex of the root canal up to and past the area of the mouth or entrance of the root canal from the interior of the tooth proper. The self-contained root canal instrument of the present invention in its range of sizes combines the functions of the prior art filling spreader tool, filling condenser tool, and the heating means. The end portion of the self-contained root canal instrument that is usable for the three operations of spreading, condensing, and heating is the plugging component. Thus, the present invention reduces not only the time and cost of filling root canals, but also reduces the armentarium necessary in the prior art.

The plugging component is provided in the aforementioned range of sizes and is provided for in a snap-in or chuck mounted method of attaching to a handle means and to a power source.

The plugging component is provided in several embodiments, each of which has a non-stick surface, such as Telfon, to prevent the filling material from adhering to the tool.

In the present invention the heating is controlled in order to stay within the range of that required for the filling material being used, so as not to under heat it and also not to char it or destroy it. In that regard, a contoured finger tip switch is conveniently located and provides for instant reheating as and if the filling material begins to cool below the workable deformation point.

Also, in the present invention the same instrument is used for softening the filling material by heat and for the compaction without withdrawing the instrument from the root canal of the patient's mouth.

In the present invention the range of sizes provides for a memory in the small sizes where it is necessary to have some flexibility in order to work around curves in the root canal. This is not possible in any of the prior art which has made attempts at a self-contained heating element.

It is, therefore, an object of this invention to provide a dental instrument for root canal work that is completely self-contained.

It is another object of this invention to provide a dental instrument for root canal work that combines the qualities and facility of a spreader and a condenser tool for lateral and vertical compacting of root canal filling material.

It is also an object of this invention to provide a dental instrument for root canal work that has a built-in means for heating the working portion of the tool.

It is a further object of this invention to provide a dental instrument for root canal work that has a range of sizes.

It is still another object of this invention to provide a dental instrument for root canal work that has a non-stick surface at the point of contact with root canal filling material.

Further objects and advantages of the invention will become more apparent in the light of the following description of the preferred embodiments.

BRIEF DESCRIPTION OF THE DRAWINGS

FIG. 1 is a pictorial view of a self-contained root canal heated condenser dental instrument;

FIG. 2 is a side view of a first embodiment of FIG. 1;

FIG. 3 is a partial top view of the plugger component of a second embodiment of a root canal dental instrument;

FIG. 4 is a partial side view of FIG. 3;

DESCRIPTION OF THE PREFERRED EMBODIMENTS

Figure 5:
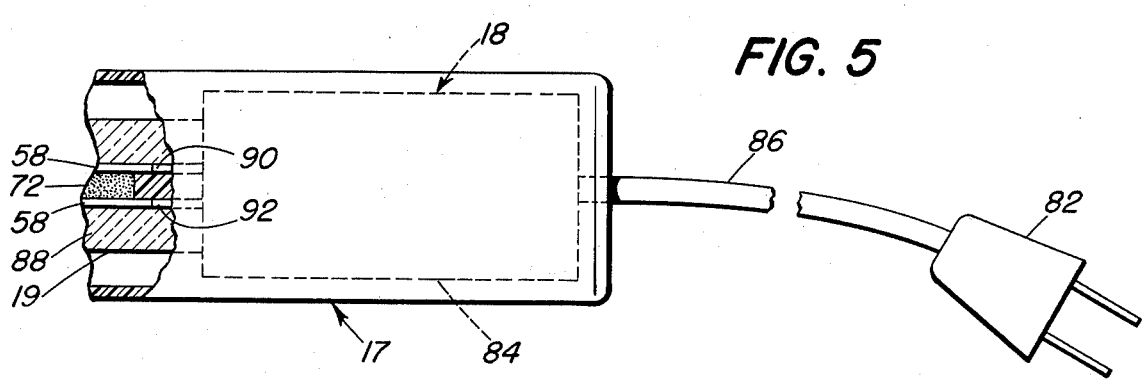
FIG. 5 is a partial side view of the power source component of a third embodiment of a root canal dental instrument.

Referring now to the drawings and particularly to FIG. 1, an improved self-contained root canal heated condenser dental instrument is shown at 15. In FIG. 1 the root canal dental instrument 15 consists of a plugger component 16 and a handle component 17. Inside the handle component 17 is a power source component 18 and a heat transmission component 19 which will be shown and described hereinafter in conjunction with other figures.

Turning now to FIG. 2, the first embodiment consists of the plugger component 16, handle component 17, power source component 18, and the heat transmission component 19. The structure of these components of the first embodiment is described hereinafter.

Figure 6:
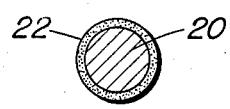
FIG. 6 is an enlarged cross sectional view on line 6—6 of FIG. 2.

The plugger component 16 on the first embodiment consists of a main core 20 with a Teflon coating 22, both as shown in FIG. 6, and other elements described hereinafter. The Teflon coating 22 extends from the end 24 of the core 20 along the tapered portion 26 of core 20 to the top 28 of the tapered portion 26. The Teflon coating 22 covers both the end 24 of the core 20 as well as the tapered portion 26.

The core 20 beyond the top 28 of the tapered portion 26 is a more or less uniform diameter for the balance of the extension, as hereinafter described, to the end that inserts into the heat transmission component 19.

The extended portion 30 is bent in a convenient goose neck like configuration to a straight portion 32 that inserts into the aforementioned heat transmission component 19. It is to be understood that the extended portion 30 may be maintained straight, bent at a right angle, or formed into any other configuration, and all such variations are within the scope and intent of the invention.

The plugger component 16, in addition to the core 20 and the Teflon coating 22, includes those portions of the core 20 described hereinbefore as the extended portion 30 and the straight portion 32.

Figure 7:
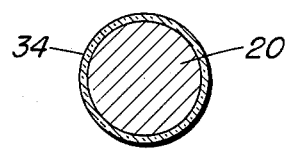
FIG. 7 is an enlarged cross sectional view on line 7—7 of FIG. 2.

The core 20 in the extended portion 30 may be insulated 34, as shown in FIG. 7, to maintain heat within the core 20 that is being conducted to the tapered portion 20. This insulation 34 also provides protection against burning of parts of the mouth of a dental patient while root canal work is being done. The insulation 34 extends from an interface with the Teflon coating 22 at the top 28 of the tapered portion 26 to a point 36 just clear of chuck 38. It is to be understood that the omission of insulation 34 is also within the scope and intent of this invention.

The core 20 may be of stainless steel, brass, chromium plated brass, or any other material that has the ability and facility to conduct heat readily.

The Teflon coating 22 prevents the root canal filling material from sticking or adhering to the plugger component 16 at the area of contact during a root canal treatment. The conducted heat, as hereinafter described, in the core 20 will readily pass through the Teflon coating 22 to heat the root canal filling material during a treatment.

The exterior portion 40 of the extended portion 30 and the straight portion 32 of the core 20 may be provided in a range of lengths in a series of plugger components 16 for use in root canal work that may vary from near the front of the mouth to the very back of the mouth. A long neck exterior portion 40 facilitates reaching the back teeth.

The insulation 34 may be any suitable insulating material that has a low conductivity of heat. It is to be understood that although the insulation 34 is shown as ending at the point 36, it may be extended through the chuck 38 so as to prevent loss of heat through the chuck 38 and also to prevent the chuck 38 from becoming hot. Such a variation is within the scope and intent of this invention.

A chuck 38 is shown as the means for connecting and holding the plugger component in place, however, it is to be understood that the straight portion 32 of the core 20 can be made as a snap-fit into the socket 42 in the heat transmission component 19 instead of using a chuck 38. A chuck 38 or a snap-fit socket 42 are known in the art and either can be used for affixing the plugger component 16 to the heat transmission component 19. If illustrated as a snap-fit type socket 42 instead of the socket 42 the illustration is substantially the same, except that the chuck 38 would be omitted. As noted, both connection and holding structures are known in the art.

The chuck 38 is affixed to the handle component 17 at an aperture in the handle component 17 through which the end of the plugger component passes to insert into the heat transmission component 19.

The handle component 17, in addition to serving as the means for a dentist to hold and use the root canal dental instrument 15 manually, also serves as a case or housing for the power source component 18 and the heat transmission component 19.

As shown in FIG. 2, the power source component 18 fits inside the end of the handle component 17 at the distal end from the plugger component 16. A simple end closure 44 provides an easy access means for inserting the power source component 18. The power source component 18 may be any available power unit 46, such as a single cell or a pair of such cells or other similar power unit, to provide a battery-like source of power. The power unit 46 used must be sufficient to provide the control heat as hereinafter described.

The power unit 46 aforementioned has a terminal means 48 at one end for transmitting power to the heat transmission component 19 as hereinafter described. The power source component 18, consists of at least one power unit 46, having the terminal means 48, and a switch means 50. The switch means 50 is a simple on-off switch of a contour configuration that is easily depressed by a finger of the hand while holding the root canal dental instrument 15 by the handle component 17.

The switch means 50 is set in the "off" position and depressing it with the finger, as hereinbefore described, turns the switch "on" to provide power to the heat transmission component 19. The switch means 50 is spring-loaded and it automatically returns to the "off" position when the finger is removed or lifted. If more than one cell is used to form the power unit 46, the arrangement is made to provide the battery-like action as is known in the art. Likewise, the switch means 50 is connected to the power unit 46 in circuit arrangement as known in the art in order to supply power to the heat transmission component 19.

The heat transmission component 19 has a terminal means 52 that interfaces and connects to the terminal means 48 of power source component 18 when the components 18 and 19 are assembled in the handle component 17. The electrical circuit then runs through the heat transmission dispensing means 54 as part of the total electrical circuit of the power source component 18 and the heat transmission component 19. Thus, when the switch means 50 is depressed the power from the power unit 46 passes through the heat transmission dispensing means 54, such as a heating coil, which then produces heat.

The heat dispensing means 54 surrounds the straight portion 32 of the plugger component 16. The heat generated and dissipated by the heat transmission dispensing means 54 passes to the straight portion 32 and is conducted through the core 20 to the tapered portion 26. The heat in the heated tapered portion 26 passes through the Teflon coating 22 for use in heating the root canal filling material, as hereinbefore described, so that the root canal dental work can be performed.

The range of sizes of the plugger component 16 may provide the range of lengths of the exterior neck 40, as mentioned hereinbefore, and may also provide a range of diameters at the small end of the tapered portion 26. The range of these small end diameters may begin with a very small diameter of less than one-half millimeter that is measured over the end of the core 20 and its Teflon coating 22.

Turning now to the second embodiment of the self-contained root canal instrument 15, the primary difference is in the structure of the plugger component 16 and the heat transmission component 19. All other components and elements of the second embodiment are substantially the same as in the first embodiment: the handle component 17, power source component 18, and the following elements—chuck 38 or the snap-in provision, end closure 44 of handle component 17, power unit 46, terminal means 48, and switch means 50. Certain other elements of the second embodiment are similar to the elements in the first embodiment, but with minor variations as will be described hereinafter.

Figure 8:
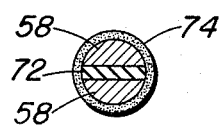
FIG. 8 is an enlarged cross sectional view on line 8—8 of FIG. 4.
Figure 9:
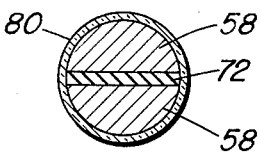
FIG. 9 is an enlarged cross sectional view on line 9—9 of FIG. 4.
Figure 10:
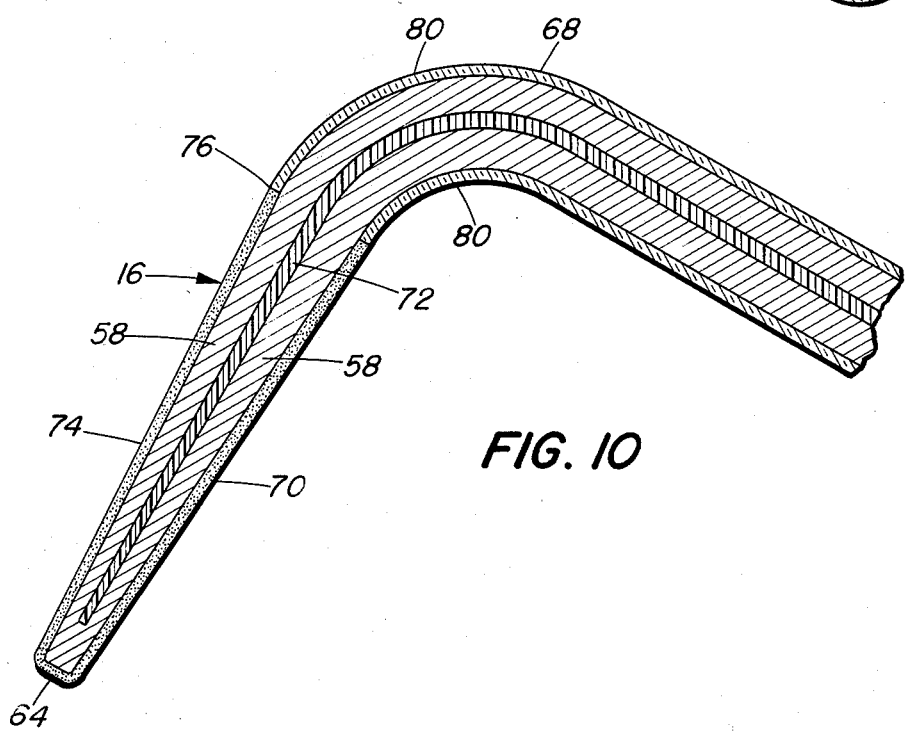
FIG. 10 is an enlarged cross sectional view on line 10—10 of FIG. 3.

Turning to FIGS. 3, 4, 8, 9, and 10, the plugger component 16 is seen in FIGS. 3 and 4, with sectional views of it in FIGS. 8, 9, and 10. The heat transmission component 19 is partially seen in FIG. 4 with other elements of it in FIGS. 8, 9, and 10.

The heat transmission component 19 consists primarily of a body member 56 and a heating element 58. The body member 56 can be seen in FIG. 4 with the heating element 58. Other cross sectional views of the heating element are shown in FIGS. 8, 9, and 10, the details of which are described hereinafter. The body member 56 is of any suitable non-conductive material, such as a thermoset plastics or other similar material.

The body 56 member of the heat transmission component 19 is affixed inside the handle component 17 in the same approximate position as the heat transmission component 19 in the first embodiment. The body member 56 has a first terminal means 60 affixed therein. The first terminal means 60 makes contact with the aforementioned terminal means 48 of the power unit 46. A second terminal means 62 in the body 56 provides the other connection to the electrical circuit of the root canal dental instrument 15, the first and second terminal means 60 and 62 of the body member 56 thus connecting the heat transmisssion component 19 of the second embodiment to the power source component 18 of the second embodiment.

The heating element 58 is the heat transmission dispensing means for the second embodiment. The heating element 58 is substantially a heating wire means that starts at its interface contact with first terminal means 60 inside the body member 56, as seen in FIG. 4. The other end of the heating element 58 is also seen in FIG. 4 making interface contact with second terminal means 62 inside the body member 56. The heating element 58 essentially makes a loop down to the end 64 of the plugger component, starting as aforementioned at first terminal means 60, running out through the straight section 66 of plugger component 16, through the chuck 38, around the gooseneck bend of the extended section 68, then down the tapered section 70, across the end 64 and up the other side of the tapered section 70, then back through the gooseneck shaped extended section 68, through the straight section 66 and making the aforementioned contact with the second terminal 62.

An insulator 72 is located between the outgoing and returning sections of heating element 58 in order to maintain the circuit. The heating element 58 in the tapered section 70 is folded and formed so as to establish the tapered section 70 configuration that is comparable to the tapered portion 26 of the core 20 of the first embodiment.

The tapered section 70 is then covered with a Teflon coating 74 in a manner similar to the Teflon coating 22 in the first embodiment. The dimensional size of the end 64 is comparable to the aforementioned dimensional size for the end 24 in the first embodiment. The Teflon coating 74 ends at the top 76 of the tapered section 70.

The exposed heating element 58 between the top 76 of the tapered section 70 and the chuck 38 is insulated 80 (and may be insulated through the chuck 80) in the same manner as the insulation 34 in the first embodiment.

The detail of the heating element 58 loop, insulator 72 between portions of the heating element 58 in the loop, the Teflon coating 74, and the insulator 80 are also shown in detail in the enlarged sectional views of FIGS. 8, 9, and 10.

In a manner similar to the first embodiment, when the switch means 50 is depressed in the second embodiment the power flows from the power unit 46 through terminals 48 and 60, then through the heating elment 58 which heats up, then through terminal 62 to complete a circuit back to the power unit 46. As in the first embodiment the heat passes through the Teflon coating 74 for use in working the root canal filling material.

Regarding the third embodiment, the only difference is in the power source component and a small modification in the heat transmission component. the third embodiment may use either the plugger component of the first or second embodiment.

Referring now to FIG. 5, the power source component 18 of the third embodiment is seen as drawing power from a commercial power source through its electrical plug 82 for an electrical receptacle.

The power source component 18 of the third embodiment consists of a regulator control unit 84, designed and set as known in the art, to maintain the flow of power at a specific range to the heating elements of the plugger components first and second embodiments, whichever is used with the third embodiment. An electrical cord 86 from the regulator control unit 84 connects to the electrical plug 82.

The heat transmission component 19 of the third embodiment is similar (with minor changes) to the heat transmission component 19 of either the first or second embodiment, depending upon which plugger component 16 is used in the third embodiment. For purposes of illustration the second embodiment arrangement is used.

A body member 88, similar to the body member 56 of the second embodiment, is modified in regard to the terminals 60 and 62 of the second embodiment. First and second terminals 90 and 92 from the regulator control unit 84 plug directly into the body member 88 to interface and connect with the aforementioned ends of the heating element 58. Separately (not shown) the switch means 50 is connected into the circuit of the regulator control unit 84 to interrupt the circuit, and to complete the circuit when the switch means 50 is depressed.

It is to be noted that the manner of electrically connecting the regulator control unit 84 to the portion of the electrical circuit in the body member 88 and to the switch means 50 may be accomplished in numerous ways, all of which are within the scope and intent of the present invention.

It is to be noted that the extremely small size of a portion of the range of sizes of the plugger component 16 makes them flexible for following the curves of a root canal to spread and/or condense root canal filling material. These small size plugger components 16 have a memory for returning to their original configuration.

As can be readily understood from the foregoing description of the invention, the present structure can be configured in differenct modes to provide the ability to heat, spread, and condense root canal filling material in a root canal plugging and sealing operation.

Accordingly, modifications and variations to which the invention is susceptible may be practiced without departing from the scope and intent of the appended claims:

What is claimed is:

1. A self-contained root canal heated condenser dental instrument, comprising:

a handle means, said handle means being hollow, said hollow handle means having an aperture at one end and being open at the opposite end, said handle means having a removable closure means for said open end;

a power source means, said power source means being affixed inside said hollow handle means;

a dental tool means, said dental tool means being used for filling root canal cavities, said dental tool means having a first end and a second end thereof, said first end being tapered, flexible, and having a memory, said first end being capable of spreading and condensing root canal filling material, said dental tool means being capable of being heated in order to heat said root canal filling material to cause it to be workable, said dental tool means being heated by a heating element means, said heating element means being folded upon itself to form a return loop configuration of two legs, said heating element means at the apex of said return loop being further configured into said taper;

an insulating means, said insulating means being located and placed within said dental tool means and between said two legs of said return loop, said insulating means insulating each said leg electrically from the other leg;

a coating material, said coating material being applied on said tapered portion of said heating element, said coating material preventing said root canal filling material from adhering thereto;

a heat transmission means, said heat transmission means being affixed inside said hollow handle means adjacent to said aperture therein, said heat transmission means being electrically connected to said power source means, said dental tool means having said second end thereof inserted through said aperture in said handle means and into said heat transmission means, said heat transmission means drawing power from said power source means and in turn heating said first end of said dental tool means through said heating element means.

2. A self-contained root canal heated condenser dental instrument as recited in claim 1, wherein said hollow handle means is used for holding said dental instrument manually and manipulating it for root canal filling.

3. A self-contained root canal heated condenser dental instrument as recited in claim 1, and additionally, a chuck means, said chuck means being affixed to said handle means on the outside thereof and centered over said aperture therein, said chuck means being used to hold said dental tool means in position when inserted into said heat transmission means.

4. A self-contained root canal heated condenser dental instrument as recited in claim 1, and additionally, a switch means, said switch means being located and affixed on the outside of said handle means, said switch means being operable by depressing with one finger, said switch means being used in an electrical circuit through which said heat transmission means draws said power from said power source means, said switch means maintaining an off position in said electrical circuit until said switch means is depressed.

5. A self-contained root canal heated condenser dental instrument as recited in claim 1, wherein said power source means is a battery means.

6. A self-contained root canal heated condenser dental instrument as recited in claim 1, wherein said power source is a commercial electrial service.

7. A self-contained root canal heated condenser dental instrument as recited in claim 6, and additionally a regulator control means to maintain power from said power source within a specific range.

8. A self-contained root canal heated condenser dental instrument as recited in claim 1, wherein said dental tool means inserted into said heat transmission means is held therein by a snap fit.

* * * * *